United States Patent [19]
Gerber

[11] Patent Number: 4,806,350
[45] Date of Patent: Feb. 21, 1989

[54] VACCINE FORMULATION

[75] Inventor: Jay D. Gerber, Lincoln, Nebr.

[73] Assignee: Norden Laboratories, Inc., Lincoln, Nebr.

[21] Appl. No.: 853,797

[22] Filed: Apr. 18, 1986

[51] Int. Cl.$^4$ .............................................. A61K 39/00
[52] U.S. Cl. ........................................ 424/88; 424/92; 514/885; 514/937; 514/943
[58] Field of Search .................... 424/88, 92; 514/885, 514/937, 938, 939, 943

[56] References Cited

U.S. PATENT DOCUMENTS 4,101,652 7/1978 Bonati ................................... 424/49

FOREIGN PATENT DOCUMENTS 109942 5/1984 European Pat. Off. .
180564 5/1986 European Pat. Off. .

OTHER PUBLICATIONS

Egerton et al., "Effect of Quil A ... ", Vet. Sci. Communic. 2(1978) 247–252.
Scott, et al., "Adjuvant ... Glycoprotein", Int. Archs Allergy Appl. Immun. 74: 373–377 (1984).
Maharaj, et al., "Immune Responses ... Saponin", Can. J. Microbiol. vol. 32, 1986.
McColm, et al., "Comparison of Saponin ... ", Parasite Immunol. 1982 4, 337–347.
Freund, Adv. Tuberc. Res. 7:130 (1956).
Dalsgaard et al., Acta vet. Scand. 18:349–360 (1977).
Bomford, Int. Arch. Allergy Appl. Immunol. 67(2): 127–131 (1982).
Charlier, et al., Arch. Exp. Vet.-Med. 27:783 (1973).

Primary Examiner—Matthew A. Thexton
Assistant Examiner—Catherine S. Kilby
Attorney, Agent, or Firm—Edward T. Lentz; Janice E. Williams; Alan D. Lourie

[57] ABSTRACT

A highly immunogenic aqueous vaccine formulation adjuvanted with a saponin and an oil.

11 Claims, No Drawings

VACCINE FORMULATION

FIELD OF THE INVENTION

This invention relates to a novel vaccine formulation shown to have enhanced immunostimulating properties.

BACKGROUND OF THE INVENTION

Early in the history of vaccine development, it was discovered that addition of foreign substances, including particulate matter, to vaccine formulations increased the immune response to such vaccines. Freund reported use of water-in-oil (W/O) emulsions to enhance antibody response to an antigen. Addition of inactivated Mycobacteria to such emulsions (Freund's complete adjuvant or CFA) further enhances the cell-mediated response and may or may not enhance the humoral response.

The efficacy of vaccine adjuvants appears to be due to a sequestering or concentrating effect on an antigen or to stimulation of an inflammatory response or to both. CFA is not practical other than in laboratory experiments because local inflammation induced by its administration is unacceptably severe. Many other vaccine adjuvants have been employed in W/O as well as in oil-in-water (O/W) emulsions. Such adjuvants include muramyl dipeptide (MDP), inorganic aluminum compounds such as $Al(OH)_3$ and surfactants such as trehalose dimycolate (TDM), lipopolysaccharide (LPS)-lipid A, certain hydrophilic block polymers and many alkyl nitrogenous compounds which are highly lipophilic and water insoluble.

Useful surfactants have a small polar region attached to a large non-polar region; they interact at the interphase of hydrophilic and lipophilic surfaces in W/O and O/W emulsions. Because such surfactants typically cannot reduce the surface tension of immiscible liquids, i.e., oil and water, to form an emulsion, emulsifying agents are generally added. Commonly employed emulsifiers are the Tweens and the Spans.

Freund, *Adv. Tuberc. Res.* 7: 130 (1956), reviews use of water-oil emulsions as adjuvants.

Saponins, or sapogenin glycosides, are a type of glycosidic surfactant widely distributed in plants. Use of various saponin preparations as vaccine adjuvants, though not in W/O or O/W emulsions, is well-known.

Quil A is a saponin isolated from the bark of *Quillaja saponaria* Molina, a tree native to parts of South America. It consists of a carbohydrate moiety in glycoside linkage to the triterpenoid, quillaic acid. Its use as a vaccine adjuvant is well established. See, for example, Dalsgaard et al., *Acta vet. Scand.* 18: 349–360 (1977).

Bomford, *Int. Arch. Allergy Appl. Immunol.* 67(2): 127–131 (1982), reports use of cholesterol-saponin complexes as vaccine adjuvants. Bonati, U.S. Pat. No. 4,101,642, discloses use of saponin-sterol complexes, for example, aescin, Polygala saponins, tomatin or digitonin complexed with cholesterol, in pharmaceutical compositions.

Charlier et al., *Arch. Exp. Vet.-Med.* 27: 783 (1973), report studies with various saponin preparations.

SUMMARY OF THE INVENTION

It has now been discovered that a vaccine antigen which is dually adjuvanted with an oil and a saponin is highly effective in stimulating an immune response in an animal. Thus, this invention, in one aspect, in a vaccine which comprises an effective non-toxic amount of an immunostimulating antigen and an immunostimulating, non-toxic amount of a saponin in a water and oil emulsion.

In another aspect, the invention is a method for preparing such vaccine and a method for stimulating an immune response in an animal which comprises internally administering a vaccine of the invention to the animal. These and other embodiments which are fully disclosed hereinbelow are further aspects of a single invention.

DETAILED DESCRIPTION OF THE INVENTION

The vaccine formulation of the invention employs a saponin and an oil as an adjuvant. It is a parenterally administerable mono- or polyvalent vaccine in which the antigen is any antigen or antigenic component for stimulating a desired immune response. Such vaccine can be, for example, a vaccine for protecting a mammal against infection, or against development of a disease state resulting from infection, by a pathogenic or opportunistic bacteria, virus, parasite or other invasive microbe or organism. Such vaccine can also be, for example, a hormone such as leutenizing hormone. In the former case, the antigen can be one or more modified or inactivated bacteria, viruses, parasites or other microbes or organisms or one or more subunits thereof or derivatives of such subunits.

The vaccine is formulated to comprise a vaccinal amount, that is, an effective, non-toxic amount of each antigen per dose in accordance with standard procedures for vaccine preparation employing an O/W or W/O emulsion. Typically, this comprises adding an immunostimulating antigen and a saponin to the oil or water phase of an oil and water emulsion prior to combining the oil and water. Usually, the antigen and saponin are added to the water. A saponin is typically added to the aqueous phase in an amount of 15 to 5000 micrograms, preferably 25 to 1000 micrograms, per dose. Any of the saponins or saponin derivatives can be used. See, e.g., Charlier et al., *Arch. Exp. Vet.-Med.* 27: 783 (1973) and Bonati, U.S. Pat. No. 4,101,652. Preferably, such saponin has lipophilic and hydrophilic regions and therefore can function as a surfactant and emulsifier. Quil A is the preferred saponin. Quil A forms micelles in aqueous solutions at concentrations as low as 0.03% and forms complexes with a wide range of antigens. It is publicly available from a variety of sources including commercial vendors, such as Superfos (Copenhagen, Denmark).

The oil phase comprises one or more parenterally tolerated oils. These include vegetable oil such as soy bean oil and peanut oil, mineral oils, such as Drakeol 6VR, animal oils such as squalene, and intermediate length ($C_{12}$ to $C_{20}$) alkanes, optionally substituted, such as hexadecane. See, for example, Murray et al., *Ann. Allergy* 30: 146 (1972). The amount of oil is up to 95% by volume. In O/W emulsions, the amount of oil is preferably 0.2 to 20%, more preferably 0.5 to 10% and in W/O emulsions the amount of oil is preferably 40 to 90%, more preferably 50 to 70%.

The compartmentalization of antigen with Quil A in an O/W or W/O emulsion is believed to make this delivery syste a potent immunostimulator. Since Quil A is an emulsifier, parts of each molecule of Quil A are lipophilic and other parts are hydrophilic. Quil A would therefore collect at the oil-water interface. The antigen, if complexed with Quil A, may also collect at this interface. If the antigen itself possesses hydrophilic and lipophilic characteristics it would be positioned at the interface regardless of whether or not it was attached to Quil A. If the antigen is entirely hydrophilic or entirely lipophilic and not attached to Quil A, it would be in the aqueous or oil phase respectively. When the antigen is in the oil phase, Quil A would be on the surface of the oil droplet. When the antigen is in the aqueous phase Quil A would either be in the water droplet with the antigen or on the surface of the water droplet. In either case, antigens and adjuvants are compartmentalized. Such compartmentalization appears to be a highly efficient method to deliver antigens and adjuvant to immune cells, particularly macrophages.

Quil A is also usually added to the aqueous phase when making W/O emulsions containing 50 to 70% oil. These emulsions are made by adding the aqueous phase while stirring into the oil phase or emulsifying with a high shear mixer emulsifier.

The immunostimulating antigen in an agent which upon internal administration to a mammal induces a humoral or cell mediated response to the antigen. It may be an attenuated or inactivated bacteria, virus or parasite or a polypeptide. The polypeptide can be, for example, an oligopeptide, a polypeptide or a protein derived from such organism or virus and optionally purified and may be glycosylated or otherwise modified. Alternatively, such antigen can be prepared by synthetic or by recombinant DNA techniques. The antigen can also be a protein of different origin, such as a hormone or a derivative thereof. Exemplary antigens are antigens which stimulate an immune response to Canine Parvovirus (CPV), Pseudorabies Virus (PSV), Feline Infectious Peritonitis Virus (FIP), *Dirofilaria immitis* and leutenizing hormone.

The vaccine formulation is administered internally, for example, intramuscularly, subcutaneously, intraperitoneally or intravenously, to a mammal in accordance with standard protocols for the antigen or antigens of choice. For a non-human mammal, the vaccine is typically administered intramuscularly or subcutaneously in a dose volume of 0.5 to 4 ml, preferably 1 to 2 ml. A typical vaccination protocol often calls for a second vaccination 2 to 6 weeks after the initial vaccination, followed by boosters at regular intervals, for example, every 1 to 2 years.

Additional excipients can be added as desired. For example, sterols have been complexed with saponins to reduce hemolysis associated with administration of saponins in aqueous solution; emulsifying agents such as Tweens and Spans are often employed in O/W or W/O emulsions; Montanide 888 is a monooleate commonly employed as an emulsifying agent. Additional agents or adjuvants, such as muramyl dipeptide, trehalose dimycolate, alumina, LPS and alkylamines, can also be comprised within the vaccine, although addition of further adjuvants would not be expected to enhance further the immune response.

EXAMPLES

The following examples are illustrative, and not limiting, of the invention. Drakeol 6VR, Peen-Drake, Chicago, was employed as the oil phase. To prepare 0.5 to 10% O/W emulsions, filtered sterilized Quil A (25–1000 μg/dose) was added to antigen in the aqueous phase. Emulsions were made by adding the aqueous phase to filter-sterilized oil while stirring or by layering the oil over the aqueous phase and emulsifying with a high shear mixer emulsifier (Silverson, Mixtronics Inc., Cleveland, Ohio).

Antigens that were combined with this Quil A emulsion were: (1) canine parvovirus; (2) pseudorabies virus subunit; (3) feline infectious peritonitis virus; and (4) *Dirofilaria immitis* (canine heartworm). The Examples demonstrate an unexpectedly, enhanced immune response when animals were vaccinated with vaccine formulations of the invention.

EXAMPLE 1

An inactivated canine parvovirus (CPV) vaccine was prepared by propagating a virulent CPV strain in a stable canine cell line, inactivating virulent virus harvested from the cell culture by treatment with beta-propiolactone (BPI) or a beta-ethylamine (BEI) and combining the inactivated virus with following adjuvants by addition to the water phase prior to emulsification: (1) Five percent mineral oil and Quil A (300 micrograms/one ml dose), or (2) a W/O emulsion containing Montanide 888 as an emulsifier. A third group contained guinea pigs vaccinated with a nonadjuvanted vaccine.

Quil A in a 5% O/W emulsion enhanced the antigenicity of CPV much more so than 5% of the emulsion without Quil A. In the latter vaccine, Montanide 888 instead of Quil A was used as the emulsifying agent. (Table 1).

In another experiment, guinea pigs vaccinated with inactivated CPV adjuvanted with the Quil A and O/W emulsion developed higher serum neutralization (SN) titers especially after the first vaccination than did guinea pigs vaccinated with either inactivated CPV adjuvanted with 5% Alhydrogel (aluminum hydroxide) or with nonadjuvanted vaccine (Table 2).

TABLE 1

Comparisons of the Adjuvanticity of a 5% Oil-in-Water Emulsion With and Without Quil A on Inactivated CPV

| Adjuvant | Guinea Pig No. | Reciprocal of Virus Neutralization Titer at 3 Week Postvaccination |
|---|---|---|
| 5% Oil Quil A[1] | 1 | 2048 |
| | 2 | 512 |
| | 3 | 2048 |
| | 4 | 1024 |
| | 5 | 2048 |
| | 6 | 512 |
| | 7 | 64 |
| Geometric Mean | | 761 |
| 5% Oil Montanide 888 | 8 | 64 |
| | 9 | 32 |
| | 10 | ≦32 |
| | 11 | ≦32 |
| | 12 | 32 |
| | 13 | 32 |
| | 14 | ≦32 |
| Geometric Mean | | ≦35 |

[1]300 μg/1 ml dose.

TABLE 2

Effect of Different Adjuvants on the Response of Guinea Pigs to Inactivated Canine Parvovirus Vaccine

| | | Reciprocal of Virus Neutralization Titer | |
|---|---|---|---|
| Adjuvant | Guinea Pig No. | 21 Days Post First Vaccination | 14 Days Post Second Vaccination |
| 5% oil Quil A[1] | 1 | 2048 | 8192 |
| | 2 | 512 | 8192 |
| | 3 | 2048 | ND |

TABLE 2-continued

Effect of Different Adjuvants on the Response of
Guinea Pigs to Inactivated Canine Parvovirus Vaccine

| Adjuvant | Guinea Pig No. | Reciprocal of Virus Neutralization Titer | |
|---|---|---|---|
| | | 21 Days Post First Vaccination | 14 Days Post Second Vaccination |
| | 4 | 2048 | 4076 |
| | 5 | 8192 | 8192 |
| | 6 | 512 | 8192 |
| | 7 | 256 | 16384 |
| Geometric Mean | | 1248 | 8192 |
| 5% Alhydrogel | 8 | 256 | 2048 |
| | 9 | 1024 | 4096 |
| | 10 | 512 | 4096 |
| | 11 | 512 | 8192 |
| | 12 | 64 | ND |
| | 13 | 128 | 2048 |
| | 14 | 256 | ND |
| Geometric Mean | | 283 | 3566 |
| None | 15 | 64 | 512 |
| | 16 | ≦64 | 4096 |
| | 17 | ≦64 | ND |
| | 18 | ≦64 | 1024 |
| | 19 | ≦64 | ND |
| | 20 | ≦64 | 2048 |
| | 21 | ≦64 | 1024 |
| Geometric Mean | | ≦64 | 1351 |

[1]300 μg/ml (dose = 1 ml)

EXAMPLE 2

A pseudorabies subunit vaccine was prepared by attentuating a strain of the virus by serial passage on an established porcine kidney cell line, fractionating cell culture medium on a lectin affinity column, eluting the vaccine antigen with alpha-mannoside and then combining the antigen with the following adjuvants, prior to emulsification: (1) Quil A, (2) Quil A and *Bordetella bronchiseptica,* and (3) a W/O emulsion containing Montanide 888 and Quil A. The pseudorabies subunit antigen adjuvanted with the W/O emulsion containing 1 mg Quil A/one ml dose stimulated much higher ELISA titers to pseudorabies virus in pigs than did Quil A alone or Quil A and Bordetella (Table 3). This adjuvant was the only adjuvant that stimulated an antibody response following the primary vaccination. This same vaccine antigen-adjuvant combination stimulated the best cell-mediated immune (CMI) response to pseudorabies antigens (Table 4). In another experiment, the W/O emulsion containing Quil A and Montanide 103 was a better adjuvant than 5% alhydrogel for inactivated pseudorabies virus. ELISA titers were much higher following first and second vaccinations and challenge (Table 5). In a further experiment, the CMI response to pseudorabies virus was also much higher in pigs inoculated with the vaccine containing the W/O emulsion with Quil A and Montanide 888 than with the vaccine containing alhydrogel (Table 6).

TABLE 3

ELISA Titers of Pigs to a Pseudorabies Virus
Subunit Vaccine Combined with Different Adjuvants

| Adjuvant | Pig No. | Reciprocal of ELISA Titer | | | | | | |
|---|---|---|---|---|---|---|---|---|
| | | Days Post First Vaccination | | | | Days Post Second Vaccination | | |
| | | 0 | 7 | 14 | 21 | 7 | 14 | 28 |
| Quil A[1] | 837 | 0 | 0 | 0 | 0 | 1620 | 540 | 60 |
| | 838 | 0 | 0 | 0 | 0 | 1620 | 1620 | 180 |
| | 839 | 0 | 0 | 0 | 0 | 1620 | 4860 | 180 |
| | 840 | 0 | 0 | 0 | 0 | 540 | 540 | 180 |
| | 841 | 0 | 0 | 0 | 20 | 1620 | 4860 | 540 |
| | 842 | 0 | 0 | 0 | 0 | 540 | 540 | 180 |
| | 843 | 0 | 0 | 0 | 0 | 180 | 180 | 60 |
| Geometric Mean | | 0 | 0 | 0 | 2 | 865 | 1012 | 154 |
| Quil A[1] Bordetella | 851 | 0 | 0 | 0 | 0 | 540 | 180 | 60 |
| | 852 | 0 | 0 | 0 | 0 | 540 | 180 | 180 |
| | 853 | 0 | 0 | 0 | 0 | 60 | 180 | 60 |
| | 854 | 0 | 0 | 0 | 0 | 540 | 540 | 60 |
| | 855 | 0 | 0 | 0 | 0 | 540 | 540 | 180 |
| | 856 | 0 | 0 | 0 | 0 | 540 | 180 | 60 |
| | 857 | 0 | 0 | 0 | 0 | 540 | 540 | 60 |
| Geometric Mean | | 0 | 0 | 0 | 0 | 394 | 288 | 82 |
| 50% Oil Quil A[1] Montanide 888 | 865 | 0 | 0 | 0 | 540 | 4860 | 4860 | 4860 |
| | 866 | 0 | 0 | 0 | 180 | 4860 | 4860 | 540 |
| | 867 | 0 | 0 | 0 | 1620 | 43740 | 14580 | 4860 |
| | 868 | 0 | 0 | 0 | 540 | 4860 | 14580 | 4860 |
| | 869 | 0 | 0 | 0 | 20 | 1620 | 4860 | 540 |
| | 870 | 0 | 0 | 0 | 0 | 4860 | 14580 | 540 |
| | 871 | 0 | 0 | 0 | 540 | 14580 | 14580 | 4860 |
| Geometric Mean | | | | | 137 | 6652 | 9105 | 1895 |

[1]1 mg Quil A per dose of vaccine.

TABLE 4

Lymphocyte Blastogenesis Response of Pigs Vaccinated With
a Pseudorabies Virus Subunit Vaccine Combined With
Different Adjuvants to Pseudorabies Virus

| Adjuvant | Pig No. | Net Disintegrations Per Minute | | | | | | |
|---|---|---|---|---|---|---|---|---|
| | | Days Post First Vaccination | | | | Days Post Second Vaccination | | |
| | | 0 | 7 | 14 | 21 | 7 | 14 | 28 |
| Quil A[1] | 837 | 20 | 408 | 160 | 1445 | 786 | 94 | 2049 |
| | 838 | 49 | 0 | 1326 | 585 | 1332 | 0 | 926 |
| | 839 | 0 | 223 | 1688 | 303 | 835 | 5852 | 1557 |
| | 840 | 337 | 0 | 164 | 311 | 2491 | 124 | 430 |

TABLE 4-continued

Lymphocyte Blastogenesis Response of Pigs Vaccinated With
a Pseudorabies Virus Subunit Vaccine Combined With
Different Adjuvants to Pseudorabies Virus

| | | Net Disintegrations Per Minute | | | | | | |
|---|---|---|---|---|---|---|---|---|
| | Pig | Days Post First Vaccination | | | | Days Post Second Vaccination | | |
| Adjuvant | No. | 0 | 7 | 14 | 21 | 7 | 14 | 28 |
| | 841 | 0 | 2481 | 2356 | 467 | 2029 | 1947 | 1285 |
| | 842 | 36 | 4409 | 2451 | 1084 | 4754 | 171 | 2980 |
| | 843 | 74 | 3614 | 3454 | 0 | 988 | 140 | 334 |
| Mean | | 74 | 1591 | 1657 | 599 | 1888 | 1190 | 1366 |
| Quil A[1] | 851 | 0 | 0 | 0 | 909 | 6757 | 46 | 728 |
| Bordetella | 852 | 0 | 0 | 287 | 0 | 5179 | 0 | 13581 |
| | 853 | 0 | 0 | 0 | 2263 | 11345 | 225 | 43 |
| | 854 | 0 | 0 | 0 | 5667 | 9945 | 929 | 672 |
| | 855 | 0 | 0 | 0 | 2721 | 6251 | 773 | 7178 |
| | 856 | 101 | 238 | 98 | 5801 | 3113 | 802 | 14134 |
| | 857 | 0 | 0 | 801 | 120 | 292 | 280 | 90 |
| Mean | | 14 | 343 | 169 | 2497 | 6126 | 436 | 5204 |
| 50% Oil | 865 | 0 | 17355 | 48778 | 1797 | 540 | 9816 | 84805 |
| Quil A[1] | 866 | 88 | 6417 | 15583 | 3586 | 27565 | 18853 | 29046 |
| Montanide 888 | 867 | 119 | 1376 | 52557 | 5275 | 30235 | 76221 | 74056 |
| | 868 | 0 | 9291 | 6718 | 6898 | 6915 | 0 | 34344 |
| | 869 | 0 | 659 | 4847 | 1216 | 9730 | 6708 | 9329 |
| | 870 | 38 | 4567 | 41979 | 1825 | 34144 | 124,420 | 74545 |
| | 871 | 0 | 4690 | 47991 | 6771 | 31519 | 78957 | 109,575 |
| Mean | | 35 | 6336 | 31208 | 3867 | 20731 | 44996 | 59386 |

[1]1 mg Quil A per dose of vaccine.

TABLE 5

ELISA Titers of Pigs Vaccinated with
an Inactivated Pseudorabies Vaccine Combined
with Two Different Adjuvants

| | | Reciprocal of ELISA Titer at Days Post | | | | | | | |
|---|---|---|---|---|---|---|---|---|---|
| | Pig | 1st Vaccination | | | | 2nd Vaccination | | Challenge | |
| Adjuvant | No. | 0 | 7 | 14 | 21 | 7 | 14 | 7 | 14 |
| Alhydrogel | 956 | Neg. | Neg. | 20 | 20 | 540 | 20 | 4860 | 14580 |
| (5%) | 961 | Neg. | Neg. | 180 | 180 | 1620 | 540 | 14580 | 14580 |
| | 964 | Neg. | Neg. | 60 | 60 | 180 | 540 | 4860 | 14580 |
| | 905 | Neg. | Neg. | 60 | 60 | 540 | 540 | 4860 | 4860 |
| | 968 | Neg. | 20 | 20 | 20 | 540 | 540 | 4860 | 4860 |
| Geometric Mean | | Neg. | 2 | 48 | 48 | 540 | 279 | 6054 | 9395 |
| 67% Oil | 952 | Neg. | Neg. | 540 | 1620 | 14580 | 14580 | 14580 | 14580 |
| Quil A[1] | 954 | Neg. | 60 | 540 | 540 | 14580 | 14580 | 14580 | 43740 |
| Montanide 103 | 955 | Neg. | 20 | 540 | 540 | 4860 | 14580 | 14580 | 43740 |
| | 959 | Neg. | 20 | 180 | 540 | 14580 | 14580 | 43740 | 14580 |
| | 960 | Neg. | Neg. | 540 | 1620 | 14580 | 14580 | 14580 | 14580 |
| Geometric Mean | | Neg. | 8 | 433 | 838 | 11704 | 14580 | 18163 | 22626 |

[1]1 mg Quil A per dose of vaccine.

TABLE 6

Lymphocyte Blastogenesis Response of Pigs Vaccinated with Either
Inactivated Pseudorabies Virus Vaccine
Combined with Two Different Adjuvants

| | | Net Disintegrations Per Minute | | | | | | |
|---|---|---|---|---|---|---|---|---|
| | Pig | Days Post 1st Vaccination | | | Days Post 2nd vaccination | | Days Post Challenge | |
| Adjuvant | No. | 7 | 14 | 21 | 7 | 14 | 7 | 14 |
| Alhydrogel | 956 | 1546 | 8547 | 287 | 1133 | 0 | 12429 | 3580 |
| (5%) | 961 | 1142 | 9391 | 4979 | 11040 | 15212 | 5937 | 9071 |
| | 964 | 4274 | 7910 | 284 | 2858 | 13950 | 4269 | 11228 |
| | 965 | 2352 | 11237 | 953 | 14647 | 29430 | 4117 | 41780 |
| | 958 | 490 | 5391 | 3330 | 21236 | 21918 | 8535 | 37196 |
| Mean | | 1961 | 8495 | 1967 | 10183 | 16503 | 7077 | 20571 |
| Killed Whole | 952 | 20074 | 77039 | 45123 | 60763 | 25930 | 10375 | 38830 |
| Virus Quil A[1] | 954 | 6508 | 97956 | 64158 | 59615 | 21567 | 14118 | 19263 |
| Drakeol oil/ | 955 | 7081 | 39984 | 20685 | 14057 | 18323 | 44796 | 22402 |
| Montanide 103 | 959 | 2152 | 28225 | 84912 | 64995 | 39485 | 49584 | 23191 |
| | 960 | 5164 | 58585 | 64816 | 77443 | 26834 | 9899 | 23272 |
| Mean | | 8196 | 60358 | 55939 | 55375 | 26428 | 23954 | 25392 |
| None | 984 | | | | | 177 | ND | ND |
| | 985 | | | | | 170 | 202 | 1145 |
| | 986 | | | | | 53 | 644 | 8489 |
| | 987 | | | | | 141 | ND | ND |
| | 988 | | | | | 7 | ND | ND |

TABLE 6-continued

Lymphocyte Blastogenesis Response of Pigs Vaccinated with Either
Inactivated Pseudorabies Virus Vaccine
Combined with Two Different Adjuvants

| | | Net Disintegrations Per Minute | | | | | |
|---|---|---|---|---|---|---|---|
| | Pig | Days Post 1st Vaccination | | | Days Post 2nd vaccination | | Days Post Challenge |
| Adjuvant | No. | 7 | 14 | 21 | 7 | 14 | 7 | 14 |
| Mean | | ND | ND | ND | ND | 110 | 423 | 4817 |

[1] 1 mg Quil A per dose of vaccine.

EXAMPLE 3

A feline infectious peritonitis (FIP) peplomer vaccine was prepared by propagating a virulent strain of FIP on an established stable cell line, fractionating the cell culture medium on a polyacrylamide gel to adsorb the vaccine antigen and eluting and combining the antigen with either Quil A in a 5% O/W emulsion, Quil A in a 67% W/O emulsion, or Quil A combined with polyol L121 in a 5% O/W emulsion, prior to emulsification. Twenty-five ug of Quil A was used in each adjuvant preparation. Quil A combined with either the 5% O/W, W/O emulsion, or 5% O/W emulsion and L121 stimulated a better antibody response as measured by ELISA to the FIP peplomer than did peplomer and Quil A alone (Table 7).

TABLE 7

Antibody Response of Cats to FIPV
Peplomer Following Vaccination with
Peplomer and Different Adjuvants

| Adjuvant | Cat No. | ELISA Absorbance [1] at 3 Weeks Post Third Vaccination |
|---|---|---|
| 5% Oil, Quil A[2] | TI3 | .961 |
| | TY1 | .903 |
| | UG4 | .682 |
| Mean | | .848 |
| Quil A[2] | TI5 | .544 |
| | TY3 | .481 |
| | TY4 | .394 |
| | UG3 | .413 |
| Mean | | .458 |
| Quil A[2], Polyol L121 5% Oil | TI2 | 1.037 |
| | TY2 | .764 |
| | UH2 | .919 |
| Mean | | .906 |
| 67% Oil, Quil A[2], Montanide 103 | TY5 | .682 |
| | UG2 | .583 |
| | UH1 | .797 |
| Mean | | .687 |

[1] Absorbance at 405 nm.
[2] 25 μg Quil A per dose of vaccine.

EXAMPLE 4

Dogs were vaccinated with canine heartworm antigens from an extract of adult heartworms adjuvanted with either 300 μg/ml Quil A and 5% oil, 300 μg Quil A and a 50% W/O Montanide 888 emulsions, Quil A, 5% oil and Polyol L121, or Quil A alone. All groups of dogs showed strong antibody responses to heartworm antigens as measured by a passive hemagglutination test (Table 8).

TABLE 8

Effect of Adjuvant, Route of Vaccination and Antigen
Concentration on the Antibody Titer of Dogs to
*D. immitis* Antigens

| | | | Geometric Mean Haemagglutination Titer[1] | | | | | | | |
|---|---|---|---|---|---|---|---|---|---|---|
| | | Antigen Concentration | Days Post First Vaccination | | | | Days Post Second[2] Vaccination | | | |
| Adjuvant | Route | ug/ml | 0 | 7 | 14 | 21 | 7 | 14 | 21 | 28 | 56 |
| Quil A[3] | Sc | 100 | 21 | 73 | 203 | 128 | 1171 | 169 | 256 | 81 | 127 |
| | Sc | 500 | 46 | 102 | 335 | 106 | 671 | 335 | 128 | 128 | 78 |
| | IM | 100 | 64 | 46 | 367 | 233 | 2130 | >876 | 305 | 323 | 274 |
| | IM | 500 | 40 | 84 | 465 | 335 | 1691 | 398 | 147 | 106 | 181 |
| 45% Oil/5% Montanide 888/ Quil A[3] | Sc | 100 | 47 | 133 | 738 | 465 | 2344 | 671 | ≧533 | 335 | 301 |
| | Sc | 500 | 37 | 73 | 369 | 133 | 1172 | 316 | 406 | 116 | 145 |
| | IM | 100 | 40 | 106 | 465 | 671 | 1861 | 641 | ≧465 | 369 | ≧409 |
| | IM | 500 | 58 | 81 | 406 | 406 | 1024 | 465 | 168 | 406 | 293 |
| 5% Oil Polyol L121 Quil A[3] | Sc | 100 | 40 | 58 | 738 | 256 | >3381 | 533 | 423 | 335 | 286 |
| | Sc | 500 | 53 | 46 | 256 | 161 | 2344 | 335 | 233 | 161 | 142 |
| | IM | 100 | 64 | 18 | 211 | 168 | 1172 | 369 | 185 | 106 | 105 |
| | IM | 500 | 37 | 46 | 266 | 84 | 930 | 161 | 67 | 553 | 47 |
| 5% Oil Quil A[3] | Sc | 40 | 20[4] | 55 | 443 | 543 | 1253 | 887 | 627 | 512 | 192 |
| | IM | 40 | 23[4] | 181 | ≧543 | ≧384 | 326 | 617 | 314 | 362 | 157 |

[1] Geometric mean of 3 dogs.
[2] Dogs were revaccinated 21 days post first vaccination.
[3] 300 μg Quil A per dose of vaccine.
[4] Geometric mean of 2 dogs.

EXAMPLE 5

A *Moraxella bovis* bacterin was prepared substantially as described by Gerber, European patent application No. 146,523. The bacterin was adjuvanted with (i) 5% Drakeol 6VR and Quil A (500 μg/ml) or (ii) with Quil A (500 μg/ml) alone. Bovine animals were vaccinated twice, two weeks apart, and then were challenged. Three out of 7 vaccinates receiving the bacterin with Quil A alone developed IBK. Only 1 out of 7 vaccinates receiving the bacterin with Quil A and oil developed IBK. Of six unvaccinated animals, four developed IBK. The bacterin adjuvanted with Quil A and oil maintained a stable homogeneous composition.

These examples demonstrate the utility of Quil A in an oil and water vaccine formulation and the enhancement in cellular and humoral immune response achievable with such formulations over other oil and water emulsions or formulations comprising other adjuvants. It is particularly surprising that such Quil A-oil formulation would induce a greater immune response than Quil A with other adjuvants, e.g., Bordetella.

The above descriptions and examples fully describe the invention and the preferred embodiments thereof. The invention, however, is not limited to the precise constructions herein disclosed but, rather, includes all modifications and improvements encompassed within the scope of the following claims.

I claim:

1. A vaccine for stimulating an immune response in an animal which comprises an effective, non-toxic amount of an immunostimulating antigen and an immunostimulating, non-toxic amount of a saponin in an oil and water emulsion.

2. The vaccine of claim 1 in which the saponin is 15 to 500 micrograms/dose of Quil A and the emulsion comprises up to 95% oil by volume.

3. The vaccine of claim 2 in which the amount of Quil A is 25 to 1000 micrograms per one ml dose and the emulsion comprises 0.2% to 20% or 40% to 90% oil, by volume.

4. The vaccine of claim 1 in which the antigen is an attenuated or inactivated bacteria, virus or parasite or a polypeptide.

5. The vaccine of claim 4 in which the antigen stimulates an immune response to CPV, PSV, FIPV, *Dirofilaria immitis* or leutenizing hormone.

6. A method of preparing a vaccine which comprises combining an immunostimulating antigen, a saponin and an oil and water emulsion such that the formulation contains an effective, non-toxic amount of the antigen and of the saponin per single vaccine dose.

7. The method of claim 6 in which the saponin is 15 to 5000 micrograms/dose of Quil A and the emulsion comprises up to 95% oil, by volume.

8. The method of claim 7 in which the saponin is 25 to 1000 micrograms/dose of Quil A and the emulsion comprises 0.2% to 20% or 40% to 90% oil, by volume.

9. The method of claim 6 in which the antigen is an attenuated or inactivated bacteria, virus or parasite or a polypeptide.

10. The method of claim 9 in which the antigen stimulates an immune response to CPV, PSV, FIPV, *Dicrofilaria immitis* or leutenizing hormone.

11. A method for stimulating an immune response in an animal which comprises internally administering to the animal the vaccine of claim 1.

* * * * *